United States Patent [19]

Odenwälder et al.

[11] 4,139,383
[45] Feb. 13, 1979

[54] DYE DIFFUSION TRANSFER EMPLOYING PYRIDINE AZO DYE

[75] Inventors: Heinrich Odenwälder, Cologne; Walter Püschel, Leverkusen; Rudolf Stolzenburg, Dusseldorf, all of Fed. Rep. of Germany

[73] Assignee: AGFA-Gevaert AG, Leverkusen, Fed. Rep. of Germany

[21] Appl. No.: 851,107

[22] Filed: Nov. 14, 1977

[30] Foreign Application Priority Data

Nov. 18, 1976 [DE] Fed. Rep. of Germany ....... 2652463

[51] Int. Cl.$^2$ .......................... G03C 7/00; G03C 5/54; G03C 1/40; G03C 1/10
[52] U.S. Cl. .......................................... 96/29 D; 96/3; 96/77; 96/99
[58] Field of Search ....................... 96/3, 29 D, 77, 99

[56] References Cited

U.S. PATENT DOCUMENTS

| B,351,673 | 1/1975 | Fleckenstein et al. | 96/77 |
| 3,424,742 | 1/1969 | Jarrett | 96/29 D |

Primary Examiner—Richard L. Schilling
Attorney, Agent, or Firm—Connolly and Hutz

[57] ABSTRACT

Non-diffusible dye-providing compounds for the dye diffusion transfer process yielding yellow to red color images of wanted absorption characteristics and improved light fastness correspond to the formula

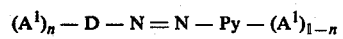

in which
 A$^1$ represents an oxidizable organic carrier residue which may be attached through a connecting member X and containing a group which confers diffusion resistance, from which carrier residue, either in its oxidized or in its unoxidized form, a part is split off together with the group which confers diffusion resistance under alkaline photographic development conditions, a diffusible azo dye represented by the formula P—N=N—B being released imagewise at the same time;
 D represents a heterocyclic or carbocyclic aromatic group;
 Py represents a pyridine or 1,2-dihydropyridine group which is attached to the azo group through its 3-position and carries an amino or hydroxyl group in its 6-position;
 n = 0 or 1.

3 Claims, No Drawings

DYE DIFFUSION TRANSFER EMPLOYING PYRIDINE AZO DYE

This invention relates to a process for the production of colour photographic images by the dye diffusion transfer process and to a photographic material suitable for this process, containing new diffusion resistant, colour providing compounds which release diffusible pyridine or 1,2-dihydropyridine azo dyes.

Among the known processes for the production of colour photographic images by dye diffusion transfer, those based on colour providing compounds which are incorporated in a diffusion resistant form and from which dyes or dye precursor products are split off in imagewise distribution in the development process to be transferred to an image receiving layer have recently become increasingly important.

Colour providing compounds suitable for these processes include, for example, the non-diffusible colour couplers described in German Patent Specification No. 1,095,115, which react with the oxidation product of a primary aromatic amine used as colour developer compound to release in a diffusible form either a preformed dye or a dye produced in the colour coupling reaction. The choice of developer compounds is, of course, in this case restricted to colour developers.

Reference should also be made in this connection to the non-diffusible colour providing compounds described in German Offenlegungsschrift No. 1,930,215, in which a preformed, latently diffusible dye residue containing a group which confers diffusion resistance is attached through a hydrazone group which can be split. These compounds should not be regarded as colour couplers and it has, moreover, been found that the choice of developer compound needed for releasing the diffusible dye residue is by no means restricted to the usual colour developers but may well be extended to black-and-white developers, for example pyrocatechols.

Non-diffusible coloured compounds have also been described in German Offenlegungsschrift No. 1,772,929. These compounds contain a special group and undergo an oxidative ring closure reaction during development to release a preformed dye residue in a diffusible form. The compounds described in this Offenlegungsschrift may be divided into two groups. The compounds of one group require a conventional colour developer compound for development. They couple with the oxidation product of this developer compound and subsequently undergo a ring closure reaction to release the preformed dye residue in a diffusible form. Compounds of the other group are themselves silver halide developers and are therefore capable, when in their oxidised form, of undergoing the above mentioned ring closure reaction to release the diffusible dyes given even in the absence of other developer compounds.

Lastly, the non-diffusible colour providing compounds described in German Offenlegungsschrift No. 2,242,762 should also be mentioned in this connection. These compounds are sulphonamido phenols and sulphonamido anilines which, after they have been oxidized by development, are decomposed under the action of the developer alkali to release diffusible dyes which have a free sulphamoyl group.

All the above mentioned colour providing compounds function negatively, i.e. when conventional (negative) silver halide emulsions are used, the imagewise distribution of the diffusible dye released from these compounds corresponds with the negative silver image produced by development. To obtain positive dye images it is therefore necessary to use direct positive silver halide emulsions or to employ a suitable reversal process.

Non-diffusible colour providing compounds disclosed in German Offenlegungsschriften Nos. 2,402,900 and 2,543,902 are capable of undergoing a splitting reaction under alkaline development conditions to release a diffusible dye but when they are in their oxidized form this splitting reaction is difficult or impossible. Such compounds may be used in combination with conventional negative emulsions to produce positive transfer colour images.

Among the known colour providing compounds, it is difficult to choose any which are satisfactory in every respect, both with regard to sufficient reactivity and with regard to sufficient stability. They should not release the diffusible dyes before alkaline development but only after imagewise oxidation has been effected by the silver halide which has been developed imagewise. On the other hand, release of the diffusible dyes either from the oxidized form of the colour providing compounds or from their non-oxidized form should proceed sufficiently rapidly and transfer of the diffusible dyes should also be rapid.

It is very important that the dyes should be fixed to a sufficient extent in the image receiving layer and, in addition, they must have excellent spectral properties and excellent stability to light and heat.

It has been observed that the dyes released from the known colour providing compounds generally do not adhere sufficiently firmly to the mordant in the image receiving layer even after neutralisation. As a result of this, the edges of the image fade out and the sharpness of the image is severely reduced, especially in monosheet materials in which the image receiving sheet carrying the coloured image is not separated from the other originally light-sensitive layers after transfer of the dyes. In extreme cases, the image obtained in the process may even disappear due to back diffusion. This is obviously undesirable.

It is therefore an object of this invention to provide new colour providing compounds for the dye diffusion transfer process, in which the diffusible dyes released during the photographic development are more firmly fixed to the mordants so that the stability and sharpness of the resulting colour transfer images are improved.

The present invention relates to a photographic dye diffusion transfer process for the production of colour images in which a photographic material having at least one light sensitive silver halide emulsion layer and a non-diffusible colour providing compound associated with it is exposed imagewise and developed in the presence of a silver halide developer so that a diffusible dye is released imagewise from the non-diffusible colour providing compound by the action of the developer alkali and transferred to the image receptor layer. In this process, the non-diffusible colour providing compound used is a compound represented by the following formula I

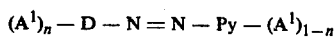

in which
$A^1$ represents an oxidizable organic carrier residue containing a group which confers diffusion resistance, from which carrier residue, either in its oxidized or in its unoxidized form, a part is split off together with the group which confers diffusion resistance under alkaline photographic development conditions, a diffusible azo dye represented by the formula D—N=N—Py in which either D or Py is modified so as to carry along with it the remaining part of the original carrier residue, being released imagewise at the same time;

D represents a heterocyclic or carbocyclic aromatic group;

Py represents a pyridine or 1,2-dihydropyridine group which is attached to the azo group at the 3-position and carries an amino or hydroxyl group in the 6-position and;

n equals 0 or 1.

The colour providing compounds according to the invention thus contain an azo dye residue of the formula D—N=N—Py which is attached to a non-diffusible, oxidizable organic carrier residue either through the group D or through the group Py. This carrier residue is such that, either in its oxidized or in its unoxidized form, it is split off from the colour providing compounds under the alkaline conditions of photographic development f.e. by hydrolysis or by an intramolecular rearrangement reaction so that a diffusible pyridine- or 1,2-dihydropyridine azo dye is released. Carrier residues $A^1$ which have such functions are already known.

Where the carrier residue $A^1$ contains a —N-H—$SO_2$—group and is connected through it to the dye the colour-providing compound is split under alkaline development conditions to release a diffusible dye carrying along with it said —NH—$SO_2$—group whereas the carrier residue left behind does no longer contain said —NH—$SO_2$—group. Therefore in this case the diffusible dye is believed to be represented by the formula:

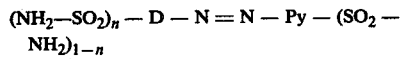

in which D, Py and n have the meanings already specified above. Thus either D or Py in fact is modified so as to carry along with it the remaining part (—N-H—$SO_2$—) of the original carrier residue.

As examples of such compounds may be mentioned, for example, the sulphonamidophenols and sulphonamidoanilines described in German Offenlegungsschrift No. 2,242,762 referred to above, which are split by the developer alkali after the oxidation reaction of development to release diffusible dyes which have a free sulphamoyl group. Other examples include the compounds described in German Offenlegungsschrift No. 2,505,248 (and the corresponding U.S. patent application Ser. No. 654,887, filed Feb. 2, 1976) and in our copending German Offenlegungsschrift 2,645,656 (and the corresponding U.S. patent application Ser. No. 839,374 filed Oct. 4, 1977, e.g. the 3-sulphonamidoindole compounds which, when in their oxidized form, are split in a similar manner by the developer alkali and release diffusible dyes carrying likewise a free sulphamoyl group. These compounds are therefore also able to effect a transfer of colour in the areas where development has taken place. U.S. Pat. applications Ser. No. 654,887 and Ser. No. 839,374 and the present application are commonly owned cases of different inventive entities as indicated by recorded assignments of these cases. German Offenlegungsschriften Nos. 2,402,900 and 2,543,902 should also be mentioned in this connection. Both of these Offenlegungsschriften describe colour providing compounds which undergo a splitting reaction under alkaline development conditions to release diffusible dyes from the non-oxidized form but this splitting reaction is difficult or impossible when the compounds are in their oxidized form. Compounds of this kind are therefore able to effect transfer of colour essentially only in those areas in which oxidation due to development has not taken place. They are therefore suitable for the production of positive transfer images.

Preferred compounds used according to the invention are represented by one of the following formula II and III:

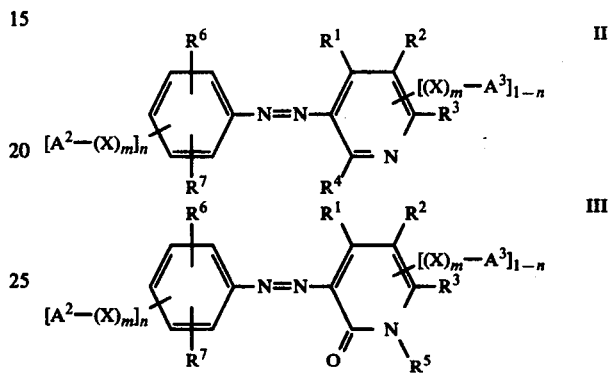

in which $A^2$ represents an oxidizable organic carrier residue in the o-, m- or p-position to the azo group, which carrier residue contains a group which confers diffusion resistance and may be attached to the compound according to the invention through a connecting member X, from which carrier residue, either in its oxidized or in its unoxidized form, a part together with the group which confers diffusion resistance is split off by the developer alkali under the conditions of photographic development, a diffusible azo dye, carrying along with it the remaining part of the original carrier residue being released imagewise at the same time;

$A^3$ represents an oxidizable organic carrier residue containing a group which confers diffusion resistance and optionally linked to the compound according to the invention through a connecting member X, which carrier residue may be contained, for example, in one of the substituents $R^1$, $R^2$, $R^3$, and $R^5$ and from which, either in its oxidized or in its unoxidized form, a part together with the group which confers diffusion resistance is split off by developer alkali under photographic development conditions, a diffusible azo dye carrying along with it the remaining part of the original carrier residue being at the same time released imagewise;

X represents a bivalent connecting member represented by the formula $R-(L)_p-(R)_q$— in which R represents an alkylene group preferably having from 1 to 6 carbon atoms or a substituted or unsubstituted phenylene group, and the two groups R may be the same as or different from each other;

L represents —O—, —CO—, —$CONR^8$—, —$SO_2N-R^8$—, —O—CO—$NH^8$—S—, —$SO_2$— or —SO— ($R^8$ = hydrogen or alkyl), p = 0 or 1, q = 0 or 1, and q = 1 when p = 1,
m,n = 0 or 1;
$R^1$ represents hydrogen, alkyl, preferably having from 1 to 4 carbon atoms, aralkyl, for example benzyl, or aryl such as phenyl;
$R^2$ represents hydrogen or an electron-attracting group, preferably a CN, —COOH, —SO$_3$H, —CONHR$^8$, —SO$_2$NHR$^8$ or —[SO$_2$—(X)$_m$]$_o$—A$^3$ group in which o = 0 or 1;
$R^3$ represents a hydroxyl group or a substituted or unsubstituted amino group;
$R^4$ represents hydrogen, a hydroxyl group or a substituted or unsubstituted amino group;
$R^5$ represents hydrogen, an alkyl group preferably having from 1 to 6 carbon atoms, aralkyl or aryl;
$R^6$ represents hydrogen, alkyl or —NO$_2$;
$R^7$ represents hydrogen, halogen, alkoxy, acylamino in which the acyl group is derived from aliphatic or aromatic carboxylic or sulphonic acids, sulphamoyl, carbamoyl, alkylsulphonyl, arylsulphonyl, trihalogen methyl or cyan.

The amino group represented by $R^3$ or $R^4$ may be a primary amino group or an amino group substituted by one or two alkyl or aryl groups, for example, dimethylamino, hydroxyethylamino, hydroxypropylamino, methoxypropylamino, methoxyethylamino or the group NH—(X)$_m$—A$^3$.

It should be noted that the non-diffusible, oxidizable organic carrier residue may be attached either through the carbocyclic aromatic ring or through the pyridine or 1,2-dihydropyridine ring. In the latter case, i.e. if the oxidizable organic carrier residue is attached to the azo dye residue of the formula D—N=N—Py through the pyridine or 1,2-dihydropyridine ring, it is preferably situated in one of the substituents $R^1$, $R^2$, $R^3$ and $R^5$. For example, the residue $R^2$ may be the group —SO$_2$—X-—A$^3$ or the group A$^3$ itself where this group A$^3$ contains a —SO$_2$—group such as in the case of A$^4$ mentioned hereinafter. Another possibility of attaching the carrier residue consists, for example, in having $R^3$ or $R^4$ consisting of the group —NH—(X)$_m$—A$^3$. If the oxidizable organic carrier is present in substituent $R^5$, the latter may consist, for example, of an alkyl group substituted by the group —(X)$_m$—A$^3$. However, the pyridine or 1,2-dihydropyridine group in the colour providing compound according to the invention must not contain more than one non-diffusible, oxidizable organic carrier residue.

Particularly preferred compounds according to the present invention are represented by the following formulae IV and V

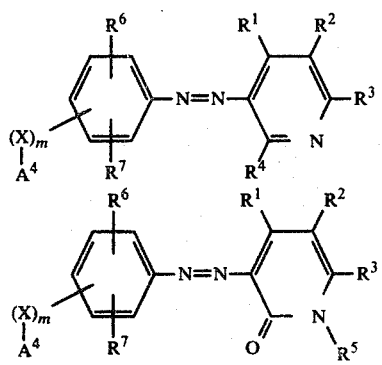

in which the symbols $R^1$, $R^2$, $R^3$, $R^4$, $R^5$, $R^6$, $R^7$, X and m having the meanings already specified and A$^4$ represents a group of one of the following formulae substituted by at least one group which confers diffusion resistance:

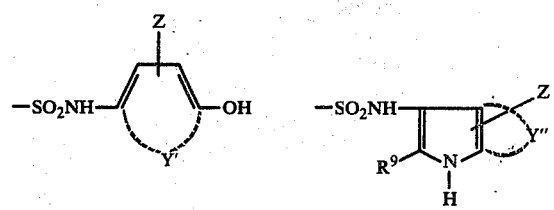

in which
Z represents a group which confers diffusion resistance,
Y' represents a group required for completing a benzene or naphthalene ring,
Y" represents a group required for completing a condensed, carbocyclic or heterocyclic ring which may be substituted and
$R^9$ represents hydrogen or an alkyl, aryl, heterocyclic, carboxyl, carbamoyl or alkoxycarbonyl group.

In the preferred embodiment of the present invention, therefore, A$^4$ represents a non-diffusible, oxidizable organic carrier residue of the kind which is split by developer alkali only when it is in its oxidized form. Dye diffusion therefore occurs only in those areas of the photographic material where the silver halide is developed.

The bivalent connecting member X represented in the general formulae II to V may consist, for example, of a group represented by one of the following formulae:

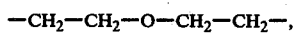

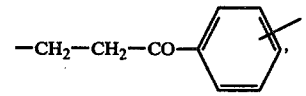

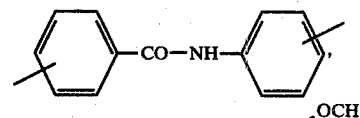

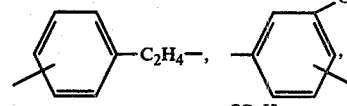

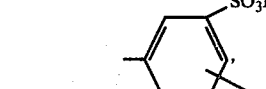

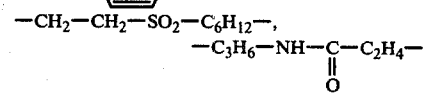

It should be noted that when the colour providing compounds according to the invention are present as intact molecules, they should not diffuse through the layers of the photographic material. For this purpose, they contain a group which confers diffusion resistance, e.g. the group Z.

The colour providing compounds may have sufficient resistance to diffusion even when they do not contain longer alkyl groups since the molecule may be sufficiently large even under these conditions, depending on the size of the dye residue. Otherwise, the colour providing compounds may be rendered resistant to diffusion by using sufficiently large groups for conferring diffusion resistance.

Groups which confer diffusion resistance are groups which make it possible for the compounds according to the invention to be incorporated in a diffusion resistant form in the hydrophilic colloids normally used in photographic materials. Organic groups generally having straight or branched chain aliphatic groups and which may also have isocyclic, heterocyclic or aromatic groups with generally from 8 to 20 carbon atoms are particularly suitable for this purpose. These groups are attached to the remainder of the molecule either directly or indirectly, e.g. through one of the following groups: —NHCO—; —NHSO$_2$—; —NR—, in which R represents hydrogen or alkyl; —O— or —S—. The group which confers diffusion resistance may, in addition, contain groups which confer solubility in water, e.g. sulpho or carboxyl groups, and these may also be present in anionic form. Since the diffusion properties depend on the size of the molecular as a whole, it is in some cases sufficient, for example if the whole molecule is large enough, to use short chain groups for conferring diffusion resistance.

The following are examples of suitable colour providing compounds according to the present invention:

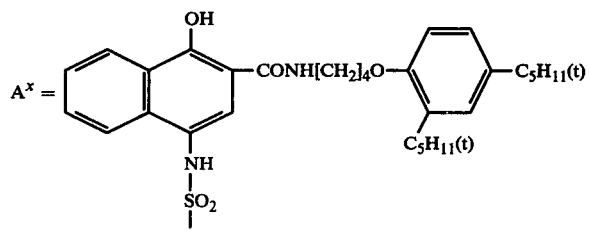

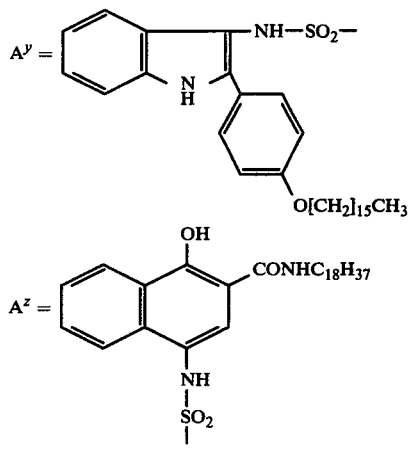

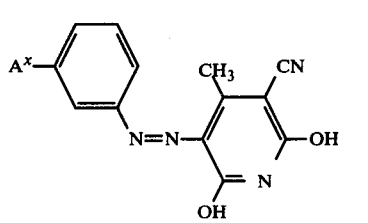

Compound 1

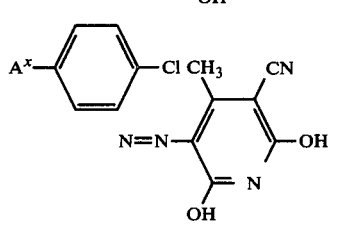

Compound 2

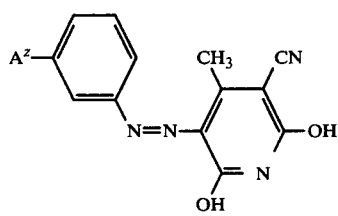

Compound 3

-continued
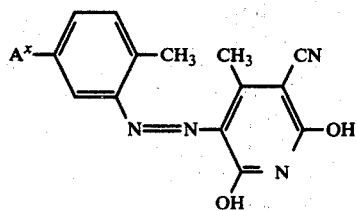
Compound 4
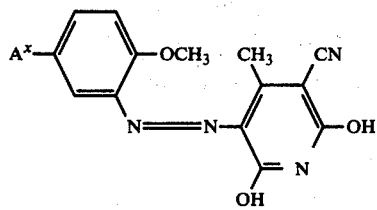
Compound 5
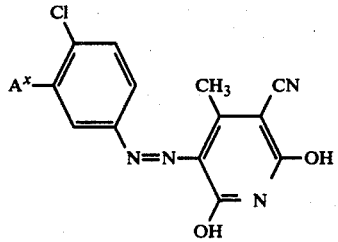
Compound 6
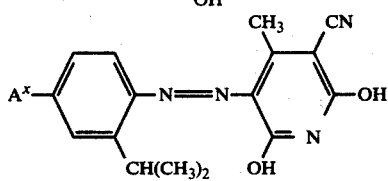
Compound 7
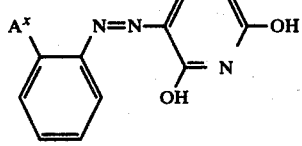
Compound 8
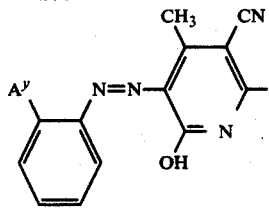
Compound 9
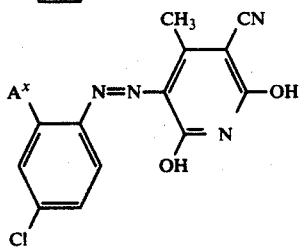
Compound 10
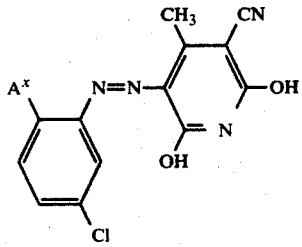
Compound 11

-continued
Compound 12
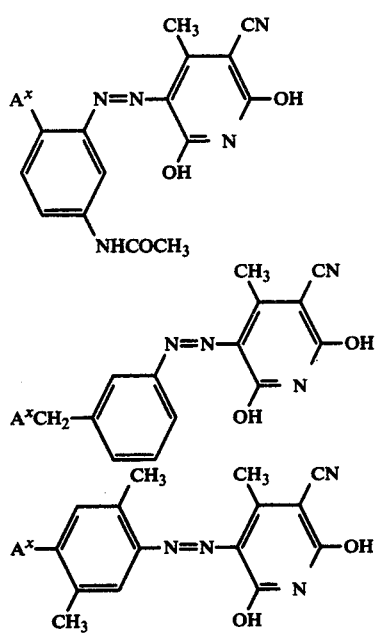
Compound 13
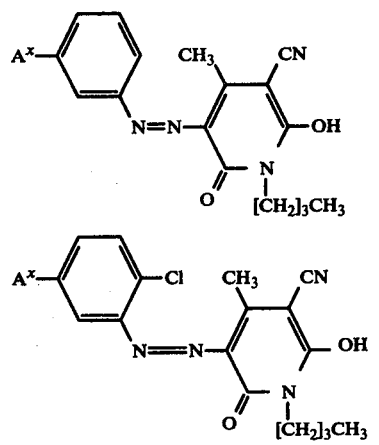
Compound 14
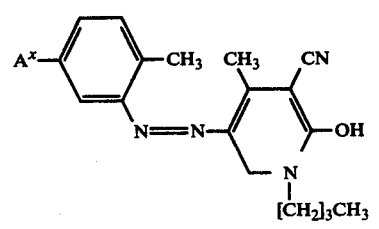
Compound 15
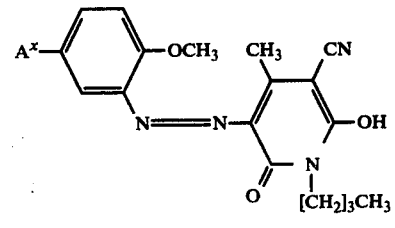
Compound 16
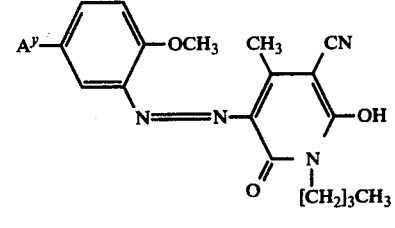
Compound 17
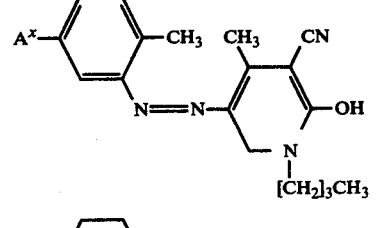
Compound 18
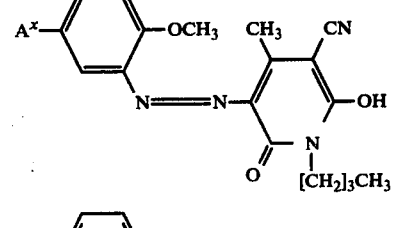
Compound 19
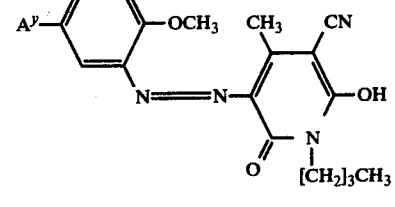

-continued
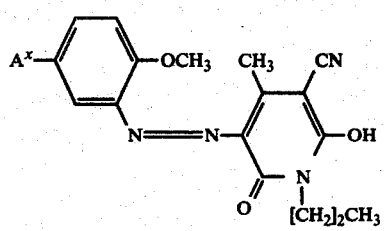
Compound 20
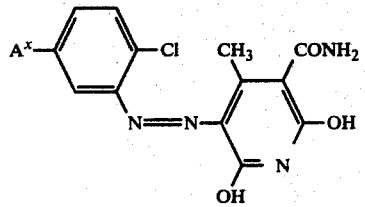
Compound 21
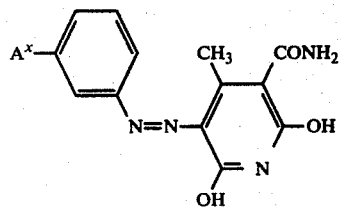
Compound 22
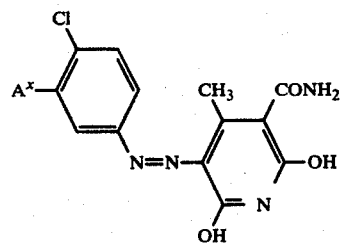
Compound 23
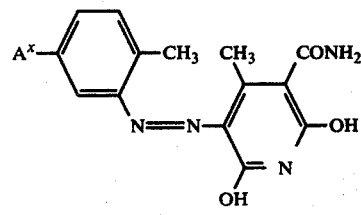
Compound 24
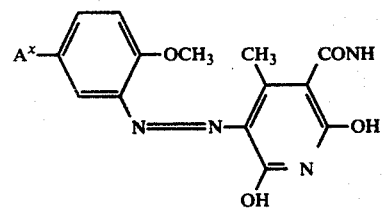
Compound 25
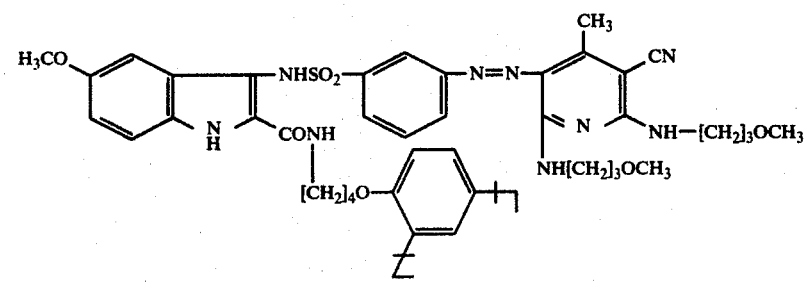
Compound 26

-continued

Compound 27

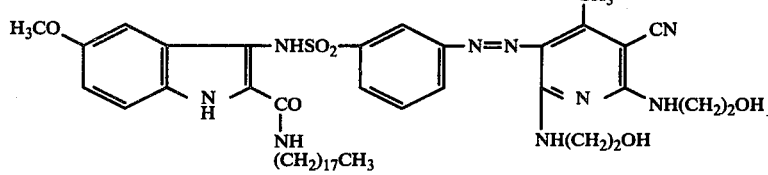

The colour providing compounds according to the invention are generally prepared from a suitably substituted aniline corresponding to the group D in the general formula I, which is diazotised and coupled to a suitably substituted pyridine derivative. The resulting azo dye may, for example, be converted into a sulphochloride derivative by known methods, which derivative is subsequently reacted with the amino group of a suitable oxidizable carrier residue. The method of preparation of compound 9 is described in detail below. The other colour providing compounds according to the present invention may be prepared in a similar manner. Preparation of 2-(4-hexadecyloxyphenyl)-3-[2-(2,6-dihydroxy-4-methyl-3-cyanopyridino-5-azo)-benzenesulphamido]-indole (Compound 9) 2-(2,6-Dihydroxy-4-methyl-3-cyanopyridine-5-azo)-benzene sulphonic acid A solution of 13.8 g of sodium nitrite in 30 ml of water was added to a suspension of 34.6 g of 2-aminobenzene sulphonic acid in 300 ml of water. Concentrated hydrochloric acid was then added dropwise at 0° to 5° C. The suspension was then stirred for 20 minutes. Excess nitrite was destroyed with amidosulphonic acid. The suspension was introduced at 0° to 5° C. into a solution of 37.6 g of the potassium salt of 2,6-dihydroxy-4-methyl-3-cyanopyridine in 100 ml of water, 20 ml of hydrochloric acid and 60 ml of pyridine. The mixture was then stirred for 2 hours. The dye was subsequently suction filtered, washed with water and dried. The yield was 67 g, having a melting point above 300° C. 2-(2,6-Dihydroxy-4-methyl-3-cyanopyridino-5-azo)-benzene sulphonic acid chloride 10 g of 2-(2,6-dihydroxy-4-methyl-3-cyanopyridino-5-azo)-benzene sulphonic acid were introduced into 100 ml of thionyl chloride and 10 ml of dimethylformamide. The suspension was stirred at room temperature for 20 hours. The reaction mixture was then poured out on ice. The sulphochloride was separated by suction filtration, washed with water and dried. The yield was 7.8 g and the product melted above 285° C. with decomposition. 2-(4-Hexadecyloxyphenyl)-3-[2-(2,6-dihydroxy-4-methyl-3-cyanopyridino-5-azo)-benzene sulphonamido]-indole 3.5 g of 2-(2,6-dihydroxy-4-methyl-3-cyanopyridino-5-azo)-benzene sulphonic acid chloride were added to a solution of 4.5 g of 2-(4-hexadecyloxy)-phenyl-3-amino-indole in 45 ml of pyridine. The reaction mixture was stirred for one hour and then filtered. Water was added to the filtrate. The resulting precipitate was suction filtered and dried. The product was finely ground in a mortar and stirred up four times with carbon tetrachloride, each time using 100 ml of carbon tetrachloride. The product was suction filtered and dried. The yield was 5.7 g, and the product melted at 218°–222° C. with decomposition.

The compounds according to the invention are yellow to red in colour.

The colour providing compounds according to the invention are incorporated in the casting solutions for the layers of photographic material by one of the usual methods. The quantity of colour providing compound used per liter of casting solution varies within relatively wide limits, and the most suitable concentration can be found with the aid of simple tests. For example, preferabyl from 5 to 80 g, more preferably from 20 to 40 g of colour providing compound may be used per liter of casting solution.

The association between diffusion resistant, colour providing compound and silver halide necessary for achieving the desired effect can be obtained, for example, by making use of the water-solubilizing groups to introduce the diffusion resistant compounds into the casting solutions from aqueous alkaline solution. Alternatively, the non-diffusible colour providing compounds may be incorporated in the layers by one of the known emulsification processes. Processes of this kind have been described, for example, in British Patent Specifications Nos. 791,219; 1,099,414, 1,099,415 1,099,416 and 1,099,417. It is also possible to prepare aqueous dispersions of the colour providing compound and add them to the given casting solutions. In that case, aqueous slurries of the colour providing compound are finely milled, for example by intensive stirring with the addition of sharp edged sand or by using ultrasound. According to another method, it may be desired to incorporate the colour providing compounds in the layer in the form of so-called micro-capsules together with silver halide and optionally also developer substances. In that case, two or more differently sensitized light-sensitive silver halide emulsions and the appropriate diffusion resistant compounds may be combined in a single layer in the form of so-called mixed grain emulsions, for example as described in U.S. Pat. No. 2,698,794. The non-diffusible, colour-providing compounds may be accommodated in a light-sensitive layer or in a layer adjacent thereto. A compound which releases a cyan dye, for example, is associated with the red sensitive layer, a compound releasing a magenta dye with the green sensitive layer and a compound releasing a yellow dye with the blue sensitive layer.

By "association" and "associated" is meant that the silver halide emulsion and the colour providing compound are arranged in relation to each other so that they are capable of interacting with each other to produce an imagewise correspondence between the silver image formed and the imagewise distribution of released diffusible dye.

The associated colour providing compound is preferably incorporated in the silver halide emulsion itself or in a layer adjacent to the silver halide emulsion layer, this adjacent layer being preferably situated behind, viewed in the direction of incident light during exposure, the silver halide emulsion layer. The colour providing compounds according to the invention are oxidized imagewise by developer oxidation products during development of the silver image and then undergo a splitting reaction under the influence of the developer alkali or activator alkali to release the dye residues in a diffusible form, generally as dye sulphonamides. The usual photographic developer compounds are suitable for development, provided that they are capable, when in their oxidized form, of oxidizing the colour providing compounds according to the invention.

The following are examples of suitable developers:
Hydroquinone,
N-methylaminophenol,
1-phenyl-3-pyrazolidone,
1-phenyl-4,4-dimethyl-3-pyrazolidone,
1-phenyl-4-methyl-4-hydroxymethyl-3-pyrazolidone,
aminophenols,
N,N-diethyl-p-phenylenediamine,
N-ethyl-N-hydroxyethyl-p-phenylenediamine,
3-methyl-N,N-diethyl-p-phenylenediamine,
N,N,N',N'-tetraalkyl-p-phenylenediamine such as tetramethyl-p-phenylenediamine, triethylsulphobutyl-p-phenylenediamine, 1,4-bis-pyrrolidinobenzene, and reductones.

It should be particularly noted that the choice of developer substances in the process according to the invention is not restricted to colour developers but that the usual black-and-white developers may advantageously also be used. This is to be seen as an advantage in view of the lower tendency of the latter to discoloration.

The developers may be contained in the layers of the photographic material, in which they are activated by the alkaline activator liquid, or they may be contained in the alkaline processing liquid or paste. Since some of the colour providing compounds according to the invention have developer properties, the use of auxiliary developer compounds may in some cases be dispensed with. In such cases, the colour providing compound is directly oxidized by the developable silver halide.

If the imagewise distribution of the diffusible dye released during development corresponds with the developed silver image, as is the case in colour providing compounds of the type described in German Offenlegungsschriften No. 2,242,763; 2,505,248; and 1,772,929, the production of positive coloured transfer images requires the use of direct positive silver halide emulsions or, if conventional negative emulsions are used, the application of a suitable reversal process. In the case of the colour providing compounds described in German Offenlegungsschrift No. 1,772,929, the diffusible dyes are not released directly as a result of being split by alkali but rather as a result of an intramolecular displacement reaction accompanied by ring closure. Moreover, the released dyes do not have a free sulphamoyl group as do the dyes split off from the colour providing compounds preferred according to the invention, but a sulphinic acid. However, the invention is by no means restricted to those colour providing compounds in which splitting is effected by alkali.

A reversal process of this kind is provided in the silver salt diffusion process. Photographic reversal by the silver salt diffusion process to produce positive colour images by means of conventional colour couplers has been described, for example, in U.S. Pat. No. 2,763,800. If the colour couplers are replaced by the colour providing compounds mentioned above, a light-sensitive element suitable for the dye diffusion transfer process is obtained. Such a light-sensitive element contains, for example, at least one combination of a light sensitive silver halide emulsion layer and a layer of binder associated therewith, containing development nuclei for physical development and a colour providing compound. In the development process, the exposed part of the silver halide in the light-sensitive silver halide emulsion layer is developed chemically while the unexposed part is transferred by means of a silver halide solvent into the associated layer of binder which contains development nuclei, and is physically developed there. If the developer used for physical development is one which, in its oxidized form, is capable of releasing a diffusible dye as a result of a reaction with the colour providing compound present in this layer, then diffusible dyes are formed in imagewise distribution and transferred to an image receiving layer where they form a positive colour image.

When reversal is carried out using compounds which split off development inhibitors in imagewise distribution, the light-sensitive element consists of at least one layer combination of a light-sensitive silver halide emulsion layer and a second emulsion layer which contains the colour providing compound and is developable without exposure. The light-sensitive silver halide emulsion layer is developed, for example, with colour developers, in the presence of certain compounds which release development inhibitor substances in their reaction with oxidized colour developer. The development inhibitor substances released imagewise in the light-sensitive layer diffuse into the adjacent emulsion layer which is developable without exposure, and in this layer they inhibit development imagewise. The uninhibited, positive, areas of this emulsion layer which is developable without exposure is thereby developed by the remaining developer, whose oxidation product then react with the non-diffusible colour providing compounds according to the invention to release diffusible dyes which are transferred imagewise to the image receiving element. Suitable compounds which react with colour developer oxidation products to release development inhibiting substances are, for example, the known DIR couplers (DIR = development inhibitor releasing), which are colour couplers which contain a releasable inhibitor group in the coupling position. DIR couplers of this kind have been described, for example, in U.S. Pat. No. 3,227,554.

Another group of compounds which release development inhibitors when they react with oxidation products of colour developers has been described in U.S. Pat. No. 3,632,345. These compounds are not colour couplers and release of the development inhibitors therefore does not give rise to dyes. Lastly, according to German Patent Specification No. 1,229,389, such a process could be carried out using suitably substituted, non-diffusible hydroquinone compounds which are oxidized to the corresponding quinones in their reaction with developer oxidation products and release development inhibiting mercaptans.

In principle, any direct positive silver halide emulsions which when subjected to simple development give rise to a positive silver image and an imagewise distribution of developer oxidation products corresponding to this image are suitable for use as direct positive silver halide emulsions. They include, for example, those silver halide emulsions in which exposure or chemical treatment results in a developable fog which is destroyed imagewise when exposure is carried out under certain conditions. The fog is preserved in the unexposed areas so that subsequent development results in a direct positive silver image and, corresponding thereto, an imagewise distribution of diffusible dye if a colour providing compound according to the invention is associated with the direct positive silver halide emulsion.

Another group of direct positive silver halide emulsions which are preferred according to the present invention covers the so-called unfogged direct positive silver halide emulsions in which the sensitivity to light is seated predominantly in the interior of the silver halide grains. When these emulsions are exposed imagewise, a latent image is formed, predominantly in the interior of the silver halide grains. The development of such unfogged direct positive silver halide emulsions is carried out under fogging conditions so that a fog is produced mainly in the unexposed areas and development results in a positive silver image. The unfogged direct positive silver halide emulsions are characterised in that when exposed samples are developed with a typical surface developer having the following composition:

| p-Hydroxyphenylglycine | 10 g |
|---|---|
| Sodium carbonate (cryst.) | 100 g |
| made up with water to | 1000 ml | they preferably do not give rise to a silver image or only to one of very low density whereas when they are developed with an internal nuclear developer having the following composition:

| Hydroquinone | 15 g |
|---|---|
| Monomethyl-p-aminophenol sulphate | 15 g |
| Sodium sulphite (anhydrous) | 50 g |
| Potassium bromide | 10 g |
| Sodium hydroxide | 25 g |
| Sodium thiosulphate (cryst.) | 20 g |
| made up with water to | 1000 ml | a silver image of sufficient density is obtained.

Selective fogging of unfogged direct positive emulsions which have been exposed imagewise may be carried out before or during development, by treating the emulsions with a fogging agent. Reducing agents such as hydrazine or substituted hydrazines are suitable fogging agents for this purpose. Reference may be had to U.S. Pat. No. 3,227,552, for example. The fogging agent may also be incorporated in a diffusion resistant form.

Unfogged direct positive emulsions are, for example, those which have gaps in the interior of the silver halide grain as described in U.S. Pat. No. 2,592,250, or silver halide emulsions which have a layered grain structure as described in German Offenlegungsschrift No. 2,308,239.

If the colour providing compounds according to the invention have a non-diffusible, oxidizable carrier residue of the type described in German Offenlegungsschriften Nos. 2,402,900 and 2,543,902, i.e. a carrier residue which is split by alkali only when it is in its unoxidised form whereas splitting is difficult or impossible in its oxidized form, the production of positive transfer images does not, of course, require the use of direct positive emulsions or the application of a reversal process but can be achieved with conventional negative emulsions.

The emulsions may be chemically sensitized, for example by the addition of sulphur compounds such as allyl isothiocyanate, allylthiourea or sodium thiosulphate during chemical ripening. Reducing agents may also be used as chemical sensitizers, for example the tin compounds described in Belgian Patent Specifications Nos. 493,464 and 568,687, polyamines such as diethylene triamine or aminomethanesulphinic acid derivatives, for example, according to Belgian Patent Specification No. 547,323.

Noble metals such as gold, platinum, palladium, iridium, ruthenium and rhodium and compounds of these metals are also suitable chemical sensitizers. This method of chemical sensitization has been described in the article by R. Koslowsky, Z. Wiss. Phot. 46, 65-72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols, cyclic dehydration productions of hexitols, alkyl-substituted phenols, aliphatic carboxylic acids, aliphatic amines, aliphatic diamines and amides. The condensation products should have a molecular weight of at least 700, preferably more than 1000. These sensitizers may, of course, be used as combinations to achieve special effects, as described in Belgian Patent Specification No. 537,278 and in British Patent Specification No. 727,982.

The emulsions may also be spectrally sensitized, e.g. with the usual monomethine or polymethine dyes such as acid or basic cyanines, hemicyanines, streptocyanines, merocyanines, oxonoles, hemioxonoles, styryl dyes or others, as well as trinuclear or higher nuclear methine dyes, for example rhodacyanines or neocyanines. Sensitizers of this kind have been described, for example, in the work by F. M. Hamer "The Cyanine Dyes and Related Compounds" (1964) Interscience Publishers John Wiley and Sons, New York.

The emulsions may contain the usual stabilizers, e.g. homopolar compounds or salt compounds of mercury having aromatic or heterocyclic rings, such as mercaptotriazoles, or simple mercury salts, sulphonium mercury double salts and other mercury compounds. Azaindenes are also suitable stabilisers, particularly tetra- and penta-azaindenes and especially those which are substituted with hydroxyl or amino groups. Compounds of this type have been described in the article by Birr, Z. Wiss. Phot. 47, 2-27 (1952). Other suitable stabilizers include heterocyclic mercapto compounds e.g. phenyl mercapto tetrazole, quaternary benzothiazole derivatives and benzotriazoles.

The binder used for the photographic layers is preferably gelatine although this may be partly or completely replaced by other natural or synthetic binders. Examples of natural binders include alginic acid and its derivatives such as its salts, esters or amides, cellulose derivatives such as carboxymethylcellulose, alkylcelluloses such as hydroxyethylcellulose, starch or its derivatives such as ethers or esters, or carrageenates. Polyvinyl alcohols, partially saponfied polyvinyl acetate, polyvinyl pyrrolidone and the like are examples of suitable synthetic binders.

The layers may be hardened in the usual manner, for example with formaldehyde or halogen substituted aldehydes containing a carboxyl group, such as mucobromic acid, diketones, methane sulphonic acid esters or dialdehydes.

The light-sensitive element used for carrying out the dye diffusion transfer process according to the present invention contains one or more silver halide emulsion layers and the non-diffusible colour providing compounds associated therewith, and an image receiving element in which the desired colour image is produced by the diffusible dyes which are transferred to it imagewise. To effect this transfer, firm contact must be established between the light-sensitive element and the image receiving element for at least a finite period of time during development so that the imagewise distribution of diffusible dyes produced in the light-sensitive element as a result of development can be transferred to the image receiving element. This contact may be established either after development has begun or even before development. The latter method may be employed, for example, in cases where the light-sensitive element and the image receiving element in the material used for carrying out the dye diffusion transfer process form an integral unit, hereinafter referred to as monosheet material, which is preserved even after completion of the development process, i.e. the light-sensitive element is not separated from the image receiving element even after colour transfer. Such an arrangement has been described, for example, in German Offenlegungsschrift No. 2,019,430.

A monosheet material suitable for carrying out the dye diffusion transfer process according to the present invention may comprise, for example, the following layer elements:
(1) a transparent support layer
(2) an image receiving layer
(3) a light impervious layer
(4) a light-sensitive element having at least one light-sensitive silver halide emulsion layer and at least one non-diffusible colour providing compound associated with this layer,
(5) a retarding layer,
(6) an acid polymer layer,
(7) a transparent support layer.

The elements of the monosheet material may be so arranged that two different parts are prepared separately from each other, namely the light-sensitive part (layer elements 1 to 4) and the cover sheet (layer elements 5 to 7), these two parts being then placed together with their active surfaces in contact and bonded together, optionally with the interposition of spacer strips so that a space is left between the two parts for an accurately calculated quantity of processing liquids. The layer elements 5 and 6, which together form the neutralisation system, may also additionally or alternatively be arranged between the substrate and the image receiving layer of the light-sensitive part, but in this case their sequence would be reversed.

Means may be provided for introducing a processing liquid between the light-sensitive part and the cover sheet, for example in the form of a rupturable container arranged at the side of the material so that it pours out its contents between two adjacent layers of the monosheet material when subjected to mechanical forces.

An essential part of the photographic material according to the present invention is the light-sensitive element which, in the case of a single dye transfer process, contains a light-sensitive silver halide emulsion layer and a non-diffusible colour providing compound associated therewith. This non-diffusible compound may be situated in a layer adjacent to the silver halide emulsion layer or in the silver halide emulsion layer itself. In the latter case, the colour of the image dye is preferably chosen so that the predominant absorption range of the colour providing compound does not correspond with the predominant sensitivity range of the silver halide emulsion layer.

To produce multicoloured transfer images in true-to-life colours, the light-sensitive element contains three such associations of colour providing compound with light-sensitive silver halide emulsion layer, and the absorption range of the colour providing compound as a rule substantially corresponds to the range of spectral sensitivity of the associated silver halide emulsion layer. In that case, in order to obtain the highest possible sensitivity it is necessary that the colour providing combination should be arranged in a separate layer of binder behind, viewed in the direction of incident light during exposure, the silver halide emulsion layer.

The action of the developer oxidation products produced by development of the silver halide emulsion must, of course be restricted to the associated colour providing compounds. Separating layers are therefore generally provided in the light-sensitive element to prevent diffusion of the developer oxidation products into other layers with which they are not associated.

These separating layers may, for example, contain suitable substances which react with the developer oxidation products, for example, non-diffusible hydroquinone derivatives or, if the developer is a colour developer substance, non-diffusible colour couplers. In a preferred arrangement, therefore, the light-sensitive element has the following arrangement of components, from below upwards:
blue sensitive silver halide emulsion layer,
layer containing non-diffusible compound which releases a diffusible yellow dye,
separating layer,
green sensitized silver halide emulsion layer,
layer containing non-diffusible compound which releases a diffusible magenta dye,
separating layer,
red-sensitized silver halide emulsion layer,
layer containing non-diffusible compound which releases a diffusible cyan dye.

The silver halide emulsion layers may, of course, also be arranged in a different sequence, but in that case the associated layers containing the colour providing compounds must also be interchanged so that the association is preserved.

The light impervious layer arranged under the light-sensitive element is permeable to aqueous alkaline treatment solutions and hence to diffusible dyes. It has two main functions: first, it serves to cover the image silver left in the originally light-sensitive element after development as well as the colour providing compounds left behind as colour negative so that when the photographic material is viewed through the transparent support layer of the light-sensitive part, only the positive colour transfer image is visible; second, it provides a lightproof cover for the light-sensitive element on the side facing the image receiving layer from the bottom. The latter is particularly important in cases where the monosheet material is brought into contact with the alkaline processing mass while still in the camera after exposure and is then to be pulled out of the camera to be developed outside.

Layers which are sufficiently impervious to light but sufficiently permeable to diffusible dyes may be prepared, for example, from suspensions of inorganic or organic dark pigments, preferably black pigments, for example suspensions of carbon black, in suitable binders, e.g. in gelatine solutions. To ensure adequate exclusion of light during development, it is generally sufficient to use layers from 0.5 to $2\mu$ in thickness containing from 10 to 90% by weight (based on the total dry weight) of carbon black in gelatine. The particle size of the pigment used is relatively uncritical, provided it is not substantially above $0.5\mu$.

In addition to the black pigment layer, the light impervious layer preferably also includes a white pigment layer arranged underneath it. The purpose of this white pigment layer is to cover the black layer and provide a white background for the image. Any white pigments are suitable for this layer, provided that it is not necessary to use unduly thick layers to obtain the necessary covering power. Examples of such pigments include barium sulphate, oxides of zinc, titanium, silicon, aluminium and zirconium, barium stearate and kaolin. The white pigment which is preferably used is titanium dioxide. The same conditions apply with regard to the binder, concentration and particle size as for the black pigments. The thickness of the white pigment layer may be varied according to the desired degree of whiteness of the background. Thicknesses of between 5 and $20\mu$ are preferred.

Instead of containing a light impervious layer, the monosheet material according to the present invention may contain means for producing such a layer between the light-sensitive element and the image receiving layer, for example in the form of a container for a liquid containing a clouding agent (pigment) arranged at the side of the monosheet material so that it releases its contents between the above mentioned layers when exposed to mechanical forces to form such a pigment layer between them.

The image receiving layer consists basically of a binder containing dye mordants for fixing the diffusible dyes.

The mordants used for acid dyes are preferably long chain quaternary ammonium or phosphonium compounds or ternary sulphonium compounds, e.g. those described in U.S. Patent Specifications Nos. 3,271,147 and 3,271,148. Certain metal salts and their hydroxides which react with acid dyes to form sparingly soluble compounds may also be used. The dye mordants are dispersed in the image receiving layer in one of the usual hydrophilic binders, e.g. in gelatine, polyvinyl pyrrolidone or partially or completely hydrolysed cellulose esters. Some binders may, of course, themselves function as mordants, e.g. copolymers or polymer mixtures of vinyl alcohol and N-vinylpyrrolidone, for example as described in German Auslegeschrift No. 1,130,284, or binders which consist of polymers of quaternary nitrogen bases, e.g. polymers of N-methyl-2-vinylpyridine, for example, as described in U.S. Patent Specification No. 2,484,430. Guanyl hydrazone derivatives of acyl styrene polymers such as those described in German Offenlegungsschrift No. 2,009,498, for example, are also binders which function as mordants. However, the last mentioned mordanting binders would generally be used in combination with other binders, e.g. gelatine.

The usual transparent substrate materials used in photographic practice may be used as transparent substrates for the monosheet material according to the invention, e.g. films of cellulose esters, polyethylene terephthalate, polycarbonates or other film forming polymers.

The alkaline processing substance adjusts the light sensitive material to a relatively high pH, about 11 to 14, which releases development and imagewise dye diffusion. It has been found that the dyes, and hence the images obtained, are not particularly stable at such high pH values. It is therefore necessary to adjust the material to almost neutral or slightly acid after development has been completed. This can be achieved in known manner by providing the material with an additional acid polymer layer which becomes accessible to the alkaline processing substance only gradually during development. By "acid polymer layer" is meant a layer of binder containing polymeric compounds which have acid groups, preferably sulpho or carboxyl groups. These acid groups react with the cations of the processing substance to form salts, thereby lowering the pH of the substance. The polymer compounds and hence the acid groups are, of course, incorporated in a diffusion resistant form in the said layer.

The acid polymers are in many cases derivatives of cellulose or derivatives of polyvinyl compounds, but other polymer compounds may also be used. The following are mentioned as examples of suitable acid polymers: Cellulose derivatives having a free carboxyl group, e.g. cellulose dicarboxylic acid semiesters with a free carboxyl group, such as cellulose acetate hydrogen phthalate, cellulose acetate hydrogen glutarate, ethyl cellulose acetate hydrogen succinate, cellulose acetate hydrogen succinate hydrogen phthalate, ethers and esters of cellulose which have been modified with other dicarboxylic acid anhydrides or with sulphonic acid anhydrides, for example with o-sulphobenzoic acid anhydride; carboxymethylcellulose; polystyrene sulphonic acid; polyvinylhydrogenphthalate; polyvinylacetatehydrogenphthalate; polyacrylic acid; acetals of polyvinyl alcohol with aldehydes which are substituted with carboxyl or sulpho groups, such as o-, m- or p-benzaldehyde sulphonic or carboxylic acid; partially esterified ethylene/maleic acid anhydride copolymers and partially esterified methyl vinyl ether/maleic acid anhydride copolymers.

The acid polymer layer must contain sufficient acid groups to lower the pH of the processing substance from an initial value of 11 to 14 so that the material will finally be almost neutral or slightly acid at a pH of 5 to 8.

The time delay in lowering of the pH is achieved in known manner by coating the acid polymer layer with a so-called retarding layer. This retarding layer is an alkali impermeable layer preferably consisting of a polymer which is inert to alkalies, for example a polyvinyl alcohol or a partially acetalised polyvinyl alcohol.

The amount of delay in lowering of the pH can be adjusted as desired by suitable choice of the thickness and composition of this retarding layer.

A barrier layer containing polymers having a new type of permeability behaviour has been described, for example, in German Offenlegungsschrift No. 2,455,762.

Neutralisation systems, that is to say, combinations of an acid polymer layer and a retarding layer, have been described, for example, in German Patent Specification No. 1,285,310. Layer combinations of this type may be provided in the material according to the invention, for example in the light-sensitive part, between the transparent layer substrate and the image receiving layer.

Another possible arrangement consists of placing the neutralisation system of acid polymer layer and retarding layer on the cover sheet. The two layers must, of course, be arranged in such a sequence that the alkali of the processing substance must penetrate the retarding layer before it can reach the acid polymer layer.

The dye diffusion transfer process according to the invention may advantageously be carried out in or with a suitable self-developer camera. This camera may be equipped, for example, with devices which make it possible for a solution to be distributed between the light-sensitive element and the cover sheet after exposure of the light-sensitive element, this solution serving to shield the light-sensitive material against light from the top. A camera of this kind is preferably equipped with a pair of squeezing rollers between which the monosheet material is pulled out so that the containers arranged at the side of the monosheet material are split open in their passage between the rollers and release their contents between the layers of the monosheet material.

Since the light-sensitive element is protected against unwanted exposure on both sides by light-impervious layers after it has passed between the squeezing rollers, the exposed material may be pulled out of the camera as soon as development has started.

To process the monosheet material after it has been exposed imagewise, the light-sensitive element is brought into contact with the aqueous alkaline processing solution. The silver halide emulsion layers which have been exposed imagewise are thereby developed in the presence of the developer compound, and an imagewise distribution of oxidation products of the developer compound is obtained in correspondence with the positive silver image produced, the said oxidation products of the developer compound oxidizing the associated colour providing compound, whereupon the colour providing compound releases the diffusible dye in its reaction with the alkali of the activator.

The aqueous alkaline processing solution may contain viscosity increasing additives, e.g. hydroxyethyl cellulose. It may also contain the usual development accelerators, stabilizers, silver salt solvents, fogging agents or antioxidants and other additives.

EXAMPLE OF APPLICATION

A light-sensitive element of a photographic material according to the invention was prepared by applying the following layers in succession to a transparent polyester foil used as substrate. The quantities given refer to 1 m².

(1) A mordanting layer consisting of 6 g of a polyurethane of 4,4-diphenylmethane diisocyanate, N-ethyl-diethanolamine and epichlorohydrin and 6.0 g of gelatine.

(2) A reflection layer of 24 g of titanium dioxide and 2.4 g of gelatine.

(3) A carbon black layer of 1.9 g of carbon black and 2 g of gelatine.

(4) A dye layer of 0.5 g of compound A (cyan) and 0.9 g of gelatine.

(5) A red sensitized emulsion layer containing an unfogged, direct positively functioning silver chlorobromide emulsion, silver application 2.6 g, gelatine 1.3 g. and 0,04 g of the fogging agent of formula D (6) A barrier layer of 0.5 g of octadecyl hydroquinone sulphonic acid and 1.3 g of gelatine.

(7) A dye layer of 1 g of compound B (magenta) and 1 g of gelatine, (8) A green sensitized emulsion layer having an unfogged direct positively functioning silver chlorobromide emulsion, silver application 2.5 g, gelatine 1.28 g. and 0,04 g of the fogging agent of formula D (9) A barrier layer identical to layer 6.

(10) A dye layer of 1.0 g of compound C (yellow) and 1.0 g of gelatine.

(11) A blue-sensitized emulsion layer containing an unfogged, direct positively functioning silver chlorobromide emulsion, silver application 2.7 g, gelatine 1.4 g. and 0.04 g of the fogging agent of formula D.

(12) A protective layer of 0.8 g of gelatine and 0.8 g of a compound represented by the following formula (hardener):

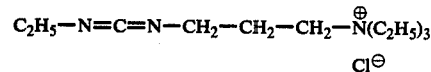

(13) A transparent cover sheet of polyethylene terephthalate comprising a neutralisation layer and a retarding layer.

After exposure through a step wedge, the light-sensitive element was covered on its active side with the transparent cover sheet. For development of the light-sensitive element after imagewise exposure, a breakable container containing an alkaline processing liquid having the following composition was used:

70 g of potassium hydroxide
10 ml of benzyl alcohol
3 g of benzotriazole
1 g of sodium sulphite
6.0 g of 1-phenyl-4-methyl-4-hydroxymethyl-3-pyrazolidone
0.1 g of hydroquinone
40.0 g of Natrosol HHR 250 (hydroxyethylcellulose), made up to 1000 ml with water.

The film set was passed through a pair of squeezing rollers, whereby the developer paste was distributed between the light-sensitive element and the cover sheet. The paste formed a layer 110μ in thickness. To adjust the thickness of this layer, spacer strips of the appropriate thickness were arranged along the edges of the image between the light-sensitive element and the cover sheet.

After a development time of 10 minutes, a direct positive, multicoloured copy of the original was obtained (film set A, comparison).

Another light-sensitive element was prepared by a similar method, the only difference being that the dye C in layer 10 was replaced by compound 19. After the same processing method, a direct positive, multicoloured copy of the original was again obtained (filmset B).

The quality of the images of filmsets A and B were then observed in some detail over a period of 8 days. In filmset A, blurring and loss of colour density were observed after only a few hours. These phenomena were caused by seeping of the mordanted dye C at the edges of the image. By contrast, the image quality of filmset 3 was unchanged after 8 days.

ANNEXE OF FORMULA TO EXAMPLE OF APPLICATION 1.

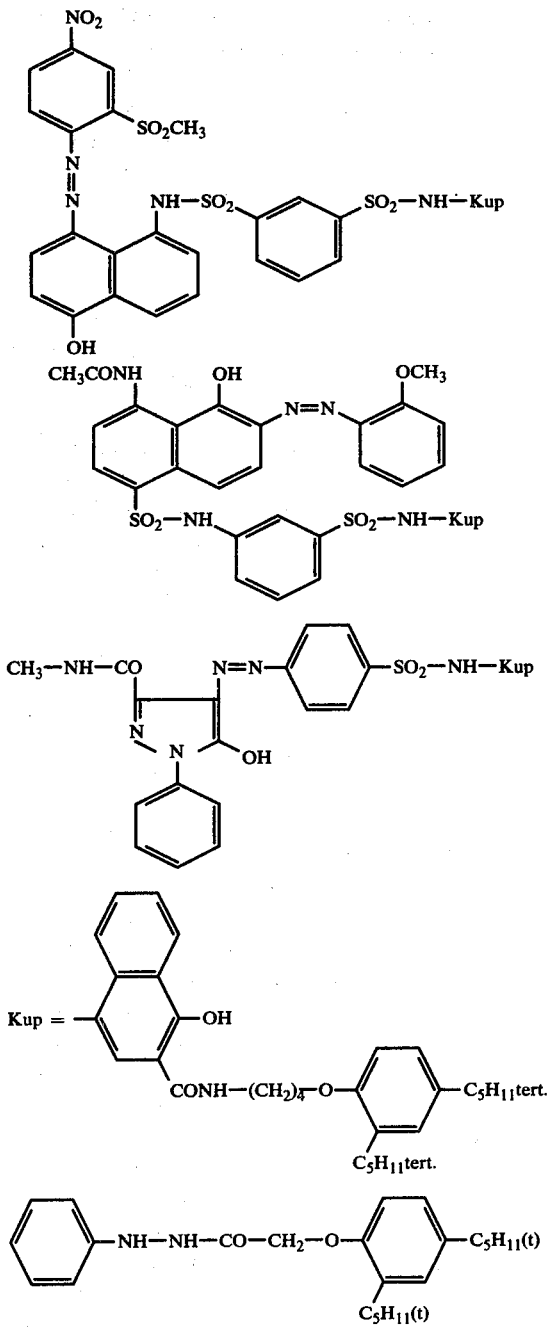

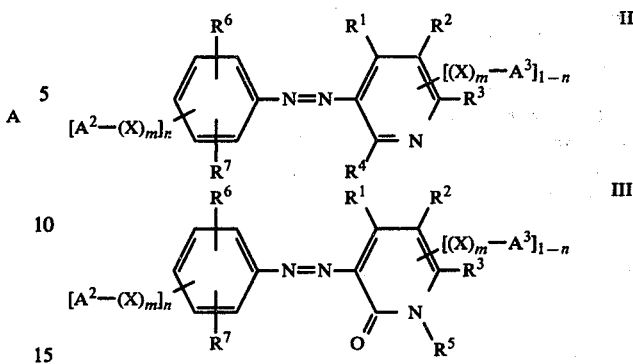

We claim:

1. A light-sensitive photographic material comprising at least one light-sensitive silver halide emulsion layer and associated therewith a non-diffusible color providing compound capable of being split under alkaline photographic development conditions either in the oxidized or in the non-oxidized form to release a diffusible dye wherein the color providing compound has one of the following formulae II and III.

in which $A^2$ represents an oxidizable organic carrier residue in the o-, m- or p-position to the azo group, which residue may be attached by way of a connecting member X and contains a group which confers diffusion resistance, from which carrier residue, either in its oxidized or in its unoxidized form, a part thereof together with the group which confers diffusion resistance is split off under the alkaline photographic development conditions, a diffusible azo dye being released imagewise at the same time;

$A^3$ represents an oxidizable organic carrier residue contained in one of the substituents $R^1$, $R^2$, $R^3$ and $R^5$, which carrier residue contains a group which confers diffusion resistance and may be attached through a connecting member X, from which carrier residue, either in its oxidized form or in its unoxidized form, a part thereof together with the group which confers diffusion resistance is split off under alkaline photographic development conditions, a diffusible azo dye being released imagewise at the same time;

X represents a bivalent connecting member having the formula $R-(L)_p-(R)_q$, in which R represents an alkylene group having up to 6 carbon atoms or a phenylene group, the two groups R being either the same or different; L represents $-O-$, $-CO-$, $-CONR^8-$, $-SO_2NR^8-$, $-O-CO-NR^8-$ $-SO_2-$, $-SO-$ or $-S-$ ($R^8$ = hydrogen or alkyl);

p = 0 or 1;
q = 0 or 1 and q = 1 when p = 1;
m,n = 0 or 1;

$R^1$ represents hydrogen, alkyl, aralkyl or aryl;

$R^2$ represents hydrogen or an electron attracting group selected from the group consisting of $-CN$, $-COOH$, $-SO_3H$, $-CONHR^8$, $-SO_2-NHR^8$ ($R^8$ = hydrogen or alkyl) and $-[SO_2-(X-)_m]_o-A^3$;

$R^3$ represents a hydroxyl group or an amino group;

$R^4$ represents hydrogen, a hydroxyl group or an amino group;

$R^5$ represents hydrogen, alkyl, aralkyl or aryl;

$R^6$ represents hydrogen, alkyl or $-NO_2$;

$R^7$ represents hydrogen, halogen, alkoxy, an acylamino group in which the acyl group is derived from an aliphatic or aromatic carboxylic or sulphonic acid, sulphamoyl, carbamoyl, alkylsulphonyl, arylsulphonyl, trihalogen methyl or cyano.

2. A material as claimed in claim 1 in which the color providing compound has one of the following formulae IV and V.

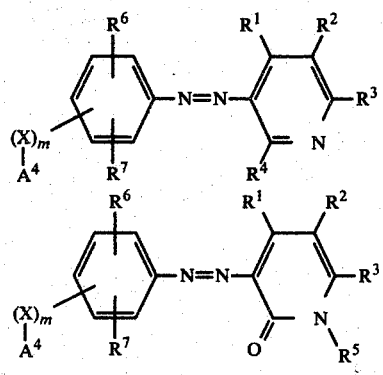

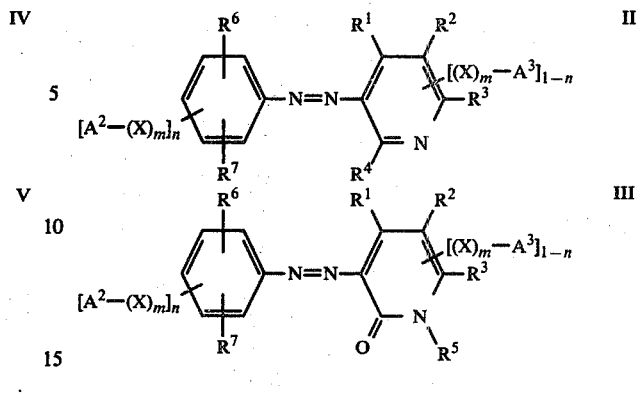

in which

R[1], R[2], R[3], R[4], R[5], R[6], R[7], X and m have the meanings specified in claim 5 and A[4] represents a residue having one of the following formulae and substituted with at least one group which confers diffusion resistance:

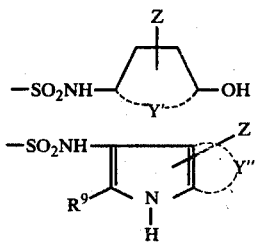

in which

Z represents a group which confers diffusion resistance,

Y' represents a group required for completing a benzene or naphthalene ring,

Y" represents a group required for completing a condensed substituted or unsubstituted carbocyclic or heterocyclic ring and R[9] represents hydrogen or an alkyl, aryl, a heterocyclic, carboxyl, carbamoyl or alkoxycarbonyl group.

3. Photographic dye diffusion transfer process for the production of color images comprising the steps of (a) imagewise exposing a photographic material having at least one light-sensitive silver halide emulsion layer and associated therewith a non-diffusible color providing compound (b) developing the material to produce therein metallic silver and developer oxidation products in image distribution (c) oxidizing said non-diffusible color providing compound with said developer oxidation products to provide image distributions of oxidized and non-oxidized color providing compound, (d) releasing under alkaline development conditions a diffusible dye either from said oxidized or said non-oxidized color providing compound and (e) transferring the diffusible dye to an image receiving layer to provide an image therein wherein the improvement comprises the non-diffusible color providing compound has one of the following formulae II and III in which A[2] represents an oxidizable organic carrier residue in the o-, m- or p-position to the azo group, which residue may be attached by way of a connecting member X and contains a group which confers diffusion resistance, from which carrier residue, either in its oxidized or in its unoxidized form, a part thereof together with the group which confers diffusion resistance is split off under the alkaline photographic development conditions, a diffusible azo dye being released imagewise at the same time;

A[3] represents an oxidizable organic carrier residue contained in one of the substituents R[1], R[2], R[3] and R[5], which carrier residue contains a group which confers diffusion resistance and may be attached through a connecting member X, from which carrier residue, either in its oxidized form or in its unoxidized form, a part thereof together with the group which confers diffusion resistance is split off under alkaline photographic development conditions, a diffusible azo dye being released imagewise at the same time;

X represents a bivalent connecting member having the formula $R-(L)_p-(R)_q$, in which R represents an alkylene group having up to 6 carbon atoms or a phenylene group, the two groups R being either the same or different;

L represents —O—, —CO—, —CONR[8]—, —SO$_2$N-R[8]—, —O—CO—NH[8]— —SO$_2$—, —SO— or —S— (R[8] = hydrogen or alkyl);

p = 0 or 1;

q = 0 or 1 and q = 1 when p = 1;

m,n = 0 or 1;

R[1] represents hydrogen, alkyl, aralkyl or aryl;

R[2] represents hydrogen or an electron attracting group selected from the group consisting of —CN, —COOH, —SO$_3$H, —CONHR[8], —SO$_2$—NHR[8] (R[8] = hydrogen or alkyl) and - —[SO$_2$—(X-)$_m$]$_o$—A[3];

R[3] represents a hyroxyl group or an amino group;

R[4] represents hydrogen, a hydroxyl group or an amino group;

R[5] represents hydrogen, alkyl, aralkyl or aryl;

R[6] represents hydrogen, alkyl or —NO$_2$;

R[7] represents hydrogen, halogen, alkoxy, an acylamino group in which the acyl group is derived from an aliphatic or aromatic carboxylic or sulphonic acid, sulphamoyl, carbamoyl, alkylsulphonyl, arylsulphonyl, trihalogen methyl or cyano.

* * * * *